United States Patent [19]

Okada et al.

[11] 4,454,161

[45] Jun. 12, 1984

[54] PROCESS FOR THE PRODUCTION OF BRANCHING ENZYME, AND A METHOD FOR IMPROVING THE QUALITIES OF FOOD PRODUCTS THEREWITH

[75] Inventors: Shigetaka Okada, Nara; Sumio Kitahata, Osaka; Shigeharu Yoshikawa, Okayama; Toshiyuki Sugimoto, Okayama; Kaname Sugimoto, Okayama, all of Japan

[73] Assignee: Kabushiki Kaisha Hayashibara Seibutsu Kagaku Kenkyujo, Okayama, Japan

[21] Appl. No.: 336,941

[22] Filed: Jan. 4, 1982

[30] Foreign Application Priority Data

Feb. 7, 1981 [JP] Japan .................................. 56-17340
Feb. 7, 1981 [JP] Japan .................................. 56-17341

[51] Int. Cl.$^3$ ......................... A23L 1/195; C12Q 1/48; A21D 10/00
[52] U.S. Cl. ...................................... 426/48; 426/49; 426/549; 426/660; 426/661; 435/15; 435/97; 435/201; 435/193
[58] Field of Search ................. 426/48, 7, 44, 49, 660, 426/549, 557; 435/193, 15, 97, 201

[56] References Cited

U.S. PATENT DOCUMENTS

| | | | |
|---|---|---|---|
| 3,249,512 | 5/1966 | Bode | 426/48 |
| 3,578,462 | 5/1971 | Smerak et al. | 426/549 |
| 3,617,300 | 11/1971 | Borochoff et al. | 426/48 |
| 3,923,598 | 12/1975 | Horikoshi et al. | 426/661 |
| 3,982,042 | 9/1976 | Arden | 426/660 |
| 4,001,435 | 1/1977 | Hirao et al. | 426/660 |
| 4,254,227 | 3/1981 | Okada et al. | 435/193 X |
| 4,320,151 | 3/1982 | Cole | 426/549 |

*Primary Examiner*—Steven L. Weinstein
*Assistant Examiner*—Marianne S. Minnick
*Attorney, Agent, or Firm*—Browdy and Neimark

[57] ABSTRACT

The present invention relates to a process for the production of branching enzyme, and a method for improving the qualities of food products therewith. According to the present invention, a large amount of branching enzyme with a high specific activity can be easily obtained, and employment of the branching enzyme in food processing remarkably improves the qualities of food products without changing the desirable inherent properties of their amylaceous constituent(s); thus, said food products retain their qualities over a long period of time, prolonging extremely their shelf lives.

17 Claims, 4 Drawing Figures

PROCESS FOR THE PRODUCTION OF BRANCHING ENZYME, AND A METHOD FOR IMPROVING THE QUALITIES OF FOOD PRODUCTS THEREWITH

DETAILED DESCRIPTION OF THE INVENTION

The present invention relates to processes for the production of branching enzyme (EC 2.4.1.18), and for the production of food products, characterized in that said food products are prepared with, or added with a reaction product which can be obtained by subjecting an amylaceous substance to the action of a branching enzyme.

It has been well known that retrogradation of amylaceous substances in food products inevitably leads to a decrease in their shelf life and digestibility.

Conventionally, in an attempt to suppress such retrogradation, partial hydrolysis of the amylaceous substance with $\alpha$-amylase, and/or addition of saccharide(s) thereto have been empirically carried out in food processing. The use of the conventional methods disadvantageously deteriorates the inherent properties of the amylaceous substance(s) in said food products, e.g., adhesiveness, viscosity-imparting properties and formality, as well as increasing sweetness of the products.

The present inventors investigated processes for the production of food products containing amylaceous substance(s) to improve their qualities without deteriorating their desirable properties.

These efforts have resulted in the finding that the use of the reaction product obtained by subjecting an amylaceous substance to the action of branching enzyme, in said food products does realize the present objectives.

Branching enzyme (EC 2.4.1.18), or Q-enzyme, is a transferase which acts on some $\alpha$-1,4-linkages of linear glucan, e.g., amylose, to branch said glucan in $\alpha$-1,6-fashion as found in amylopectin or glycogen.

Although several reports on branching enzyme have been published, for example, by G. S. Drumond et al. in Eur. J. Biochem., Vol. 26, pp. 168–176 (1972), and C. Boyer et al. in Biochemistry, Vol. 16, pp. 3693–3699 (1977), they only refer to in vivo biosynthesis and metabolism of starch in potato or glycogen in *Escherichia coli*.

Particularly, the present invention relates to a process for the production of food products wherein said food products are prepared with, or added with the reaction product obtained by subjecting an amylaceous substance to the action of branching enzyme.

As to the branching enzyme usable in the present invention, any branching enzyme can be freely selected from conventional branching enzymes of various sources, e.g., those from animal, plant or microorganism, so far as the use of the reaction product, obtained by subjecting an amylaceous substance to the action of the branching enzyme, does improve the qualities of food products. Especially, a branching enzyme from microorganism of genus Bacillus, discovered by the present inventors, is suitable for the present objectives because it can be easily produced on a large-scale as well as being highly safe.

The amylaceous substance on which the branching enzyme is allowed to act is one some of whose $\alpha$-1,4-linkages are enzymatically converted into $\alpha$-1,6-fashion by the action of the branching enzyme to form a new branched structure; for example, amylaceous substances such as amylose, amylopectin, starch, dextrin, and low-molecular-weight amylose obtained by degradation of amylopectin with a debranching enzyme; and grains and tubers with a high amylaceous substance content.

As to the method by which the reaction product, obtained by subjecting an amylaceous substance to the action of the branching enzyme, is incorporated in food products, any method can be employed in the present invention so far as the present objectives are attained thereby. For example, a solution of the amylaceous substance, prepared by gelatinization and dispersion, is first subjected to the action of the branching enzyme, and then admixed without further processing or, if necessary, after concentration and/or drying, in food products. Alternatively, the amylaceous substance is first heated in the presence of the branching enzyme to effect gelatinization and enzymatic reaction simultaneously, and the resultant is then prepared into food products as desired.

With the practice of the present invention, the retrogradation of the amylaceous substance in the food products is sufficiently suppressed because the treatment of the substance using the branching enzyme, and the treatment renders satisfactory digestibility to them. Also, the treatment can improve various properties of food products, e.g., biting properties, adhesiveness, viscosity-imparting properties, formability, thickness, dispersibility and gloss, and is very effective in retaining their desirable inherent properties over a long period of time, prolonging extremely their shelf lives.

As to the food products to which the present invention is applicable, it may be one which contains amylaceous substance(s); for example, confectioneries and bakery products such as cookies, biscuits, sponge cakes, rice cakes, sweetened bakery products and breads; noodles and pasta such as buckwheat vermicelli, Chinese-style vermicelli and macaroni; fish meat sausages; and seasonings such as curry roux, and extracts of stew and soup.

In addition to the above described amylaceous substances, other amylaceous materials, e.g., grain powder or flour such as waxy rice powder, wheat flour and corn starch, can be also subjected to the action of the branching enzyme, and the resultant product can be used favorably into confectioneries and other food products.

The following descriptions illustrate several EXAMPLEs for the production of branching enzyme, and food products therewith according to the present invention.

A. PRODUCTION OF BRANCHING ENZYME

EXAMPLE A-1

Bacillus branching enzyme

The *Bacillus megaterium* 10-5 strain, used in this EXAMPLE, was isolated from a soil in Kita-ku, Osaka, Japan.

The deposition of the strain was applied on Jan. 28, 1981 to the Fermentation Research Institute, Agency of Industrial Science and Technology, Ministry of International Trade and Industry, 1-1-3, Yatabe-cho Higashi, Tsukuba-gun, Ibaragi-ken, Japan, and accepted under FERM-P No. 5859.

The following is taxonomy of the *Bacillus megaterium* 10-5 strain.

I. Morphology (a) Cell morphology:
 (i) After 24-hour cultivation on nutrient agar slant at 28° C., end-rounded rods, 1.25–1.5×2.0–4.0μ, in regular form, are observed. Cells include globules which are unstainable by the metachromatic staining method, but stainable by the fat staining method. Occasionally, short chain form or longer filiform, and/or shadow-form are observed.
 (ii) After 24-hour cultivation on glucose agar slant at 28° C., end-rounded rods, 1.5–2.0×2.0–2.5μ, in regular form, are observed. The intracellular globules are easily stainable either by fat staining or fuchsine staining method. Nearly all of the cells are slightly short, but some are in long filiform.

(b) Mobility and flagellum:
Upon 6-hour cultivation on nutrient agar slant at 28° C., cells are very motile as illustrated in the electromicrophotograph, ×10,000 (FIG. 1).

(c) Spores:
 (i) Upon cultivation on either nutrient agar slant or soil extract slant, spores are formed readily, i.e., within 1–2 days.
 (ii) Sporangia: Swelling of sporangia is hardly noted, and the formation of spores is close to the end of sporangia.
 (iii) Spore type and dimensions: ellipsoid or oval form; and 1.0–1.5×1.25–2.5μ.

(d) Gram reaction: Cells grown by 6-hour or 24-hour cultivation on nutrient agar medium at 28° C. are all gram positive.

(e) Acid fast: Cells grown by 24-hour cultivation on nutrient medium at 28° C. are not acid fast.

(f) Capsule: After 18-hour cultivation on nutrient agar medium at 28° C., phosphorus-tungstic acid staining and subsequent electromicroscopic observation confirm the shadow around the cells, suggesting the encapsulation.

(g) Metachromatic granules: negative, upon 24-hour cultivation on nutrient agar medium at 28° C. (h) Fat globules: positive, upon 24-hour cultivation on either nutrient agar medium or glucose nutrient agar medium.

II. Cultivation properties (a) Cultivation on nutrient agar slant (28° C., 5 days): Cell growth is very abundant, and forms colonies with a diameter of 4–5 mm for five days: colonies are opaque, glistening, whitish yellow, and entired rings with a smooth and raised surface. Cell content is homogenous. During the cultivation, no pigment formation is observed.

(b) Cultivation on nutrient agar slant (28° C., 5 days): On this slant, cell growth is very readily and abundant. Colonies are slightly raised rings with a translucent, sebaceous, glistening, whitish yellow, smooth, flat and filiform surface.

(c) Suspension culture on nutrient medium (28° C., 2 days): Cell growth is very abundant, and culture medium becomes very turbid within one day; occasionally, cell aggregation in granular form is observed. The turbidity almost diminishes on two day cultivation, resulting in a large amount of sediment in lamina form. Surface ring, pigment and gas formation are not observed.

(d) Agar stab culture (28° C., 5 days): Colony formation is observed around the stabbed point of agar, and cell growth in filiform is observed in the upper layer of agar.

(e) Gelatin stab culture:
 (i) After 5-day cultivation at 20° C., the medium liquefies into saccate.
 (ii) After 10-day cultivation at 28° C., the culture medium liquefies, and hardly solidifies on cooling.
 (iii) After 5-day cultivation at 28° C. on gelatin agar streak plate, a wide zone of hydrolysis is observed.

(f) Litmus and milk:
 (i) After 14-day cultivation at 28° C., litmus turns from blue to red purple; bromocresol purple, from blue to thin blue yellow; and acid formation as well as solidification is hardly observed.
 (ii) Upon cultivation on milk agar plate, a wide zone of hydrolysis is observed within short time.

(g) Cell growth on proteose-peptone acid agar:
Cell growth is abundant, and cells appear whitish yellow, and have rugose on their surface.

(h) Cell growth on glucose nutrient agar slant:
Cell growth is the same as that obtained on nutrient agar slant.

(i) Cell growth on tyrosine agar slant:
Cell growth is abundant, and the cells have rugose on their surface.

(j) Cell growth on citrate agar slant:
Cell growth is the same as that obtained on nutrient agar slant. As the cells grow, the culture medium turns to pink and alkali.

(k) Cell growth on potato plug:
Cell growth is abundant. Colonies are yellow, soft, thick and gummy, and have rugose on their surface. A small part of the colonies drops down to the bottom of test tube. Potato is decomposed, and turns to gray.

(l) Cell growth on soy bean agar slant:
Cell growth is very readily and abundant. Colonies are opaque, glistening, creamy white, raised and filiform surfaces with rugose.

(m) cell growth on glucose-aspartic acid agar slant:
Cell growth is the same as that obtained on nutrient agar slant, and colonies are white.

(n) Cell growth on tomato-yeast milk: Medium peptonizes.

III. Physiology (a) Reduction of nitrate into nitrate: positive.

(b) anaerobic production of nitrates in gas form: Cells grow without formation of gas.

(c) Production of acetyl methyl carbinol: negative.

(d) V-P reaction: negative.

(e) Production of indole: negative.

(f) Production of $H_2S$: positive.

(g) Hydrolysis of starch: positive.

(h) Utilization of citrates: positive.

(i) Utilization of ammonium salts and nitrates: both are utilized as nitrogen source.

(j) production of pigment: Yellow pigment formation is observed in the cultivation on either milk agar medium or potato plug. Cell growth on a spore-forming medium containing soil extract yields gray pigment.

(k) Production of urease: positive.

(l) Production of catalase: positive.

(m) Optimum temperature and pH for cell growth: Cells grow in a pH range of 5.5–9.3. The optimum pH for cell growth is about 7. Cells grow in a temperature range of 10°–40° C., and the optimum temperature for cell growth is about 30° C. At a temperature of 45° C. or higher, no cell growth is observed.

(n) Effect on oxygen on cell growth: Cells grow under aerobic conditions.

(o) Hugh-Leifson test (O-F test): oxidative.

(p) Acid and gas formation from saccharides: The test is carried out at 28° C. for 14 days. Acid formation is not observed with sorbitol or rhamnose, but with arabinose, xylose, glucose, sucrose, lactose, mannitol or glycerol. No gas formation from any member of the above saccharides is observed.

(q) Hydrolysis of cellulose: negative.

Based on the above described taxonomy and reference to "Bergey's Mannual of Determinative Bacteriology," 7-th and 8-th Editions, the strain is identified to be a microorganism of *Bacillus megaterium*.

IV. Enzymology of the Bacillus branching enzyme (1) Enzymatic action: Action of the branching enzyme on amylose with a polymerization degree of about 500 leads to slight increase of reducing power, but to a gradual decrease in iodine-colorization as the reaction proceeds, resulting in a decrease in 660 nm absorbance to about 10% or lower in comparison with that without the enzymatic action.

(a) After subjecting the product, obtained in (1), to the action of either Bacillus saccharifying α-amylase or poultry pancreas α-amylase, paper chromatographic analysis on the resultant product confirms the production of isomaltosyl maltose and higher branched dextrins, suggesting the production of an α-1,6-linked product from amylose wherein the glucose units are linked in α-1,4-fashion.

(b) After subjecting the product, obtained in (1), to the action of isoamylase, the resultant is then subjected to the action of a Bacillus saccharifying α-amylase. Paper chromatographic analysis on the resultant product confirms the absence of isomaltosyl maltose, suggesting that the α-1,6-linkages are hydrolyzed by isoamylase.

(c) Enzymatic action of isoamylase on the product, obtained in (1), leads to a gradual increase in iodine-colorization as the reaction proceeds, resulting in an about 1.1–10-fold increase in absorbance at 660 nm in comparison with that without the enzymatic action. This suggests the hydrolysis of the α-1,6-linkages in the product by isoamylase, and a linear dextrin formation thereby.

(d) After subjecting the product, obtained in (1), to the action of β-amylase, the degradation degree decreases to about 50% of the starting amylose, suggesting that the degradation limit by β-amylase decreases because of the newly-formed α-1,6-linkages.

(e) After subjecting the product, obtained in (1), to the action of isoamylase, the average polymerization degree of the resultant product is about 14 as determined by conventional "Terminating group method" wherein the polymerization degree is calculated with the reducing power and the total sugar. The polymerization degree is more close to that of a glycogen hydrolysate obtained with isoamylase (about 12), rather than that of an amylopectin hydrolysate obtained with isoamylase (about 21). Complete methylation of the product, obtained in (1), acid-hydrolysis and subsequent gas-liquid chromatographic analysis give an average branch length of the product, about 14 in terms of glucose units.

(2) Substrate specificity:

Besides on amylose, the branching enzyme acts on amylopectin, starch and low-molecular-weight amylose with an average polymerization degree of 18.

(3) Assay of branching activity:

After partially purifying the branching enzyme and removing α-amylase, 100 μZ of 0.1% amylose in 0.05 M phosphate buffer (pH 7.5) is added with 100 μZ of the enzyme solution, and the mixture is then incubated at 25° C. for 10 minutes. To the reaction mixture is added 3 ml of 1/300 N iodine solution, consisting of 0.004 M KI and 0.005 N HCl, and the absorbance of the mixture is determined at a wave length of 660 nm. One unit of branching activity is defined as the amount of enzyme that decreases 660 nm absorbance by 0.1% per minute under the above described conditions. This assay method can be applied when the branching enzyme is contaminated with α-amylase, provided an amylase inhibitor which does not inhibit the activity of the branching enzyme, e.g., that produced by genus Streptomyces (S. Ueda et al., Agr. Bio. Chem., Vol. 37, No. 9, pp. 2025–2030 (1973)), is used simultaneously.

(4) pH optimum and pH stability:

At a pH in the range of 4–6, acetate buffer is used; phosphate buffer, pH 6–8; and glycine-NaOH buffer, pH 8–10. The pH optimum is determined by the above assay method, wherein the amylose solution is adjusted to different pH levels. The pH stability is determined first by incubating the enzyme solution at different pH levels at 25° C. for 25 hours, then assaying the residual activity after pH-adjustment to 7.5. The results are given in FIG. 2. The pH optimum is about 7.6, and the enzyme is stable in a pH range of 6.5–8.5.

(5) Temperature optimum and thermal stability:

The temperature optimum is determined according to the above described assay method, wherein incubation is carried out at different temperature. The thermal stability is determined first by incubating the enzyme solution at pH 7.5 and different temperature for 10 minutes, then assaying the residual enzymatic activity at 25° C. The results are given in FIG. 3. The temperature optimum is about 25° C., and the enzyme is stable at a temperature up to about 45° C.

(6) Inhibition, activation and stabilization of the branching enzyme: The activity of the branching enzyme is inhibited by the presence of $2.5 \times 10^{-3}$ M zinc, mercury or cadmium ion. Also, the presence of $10^{-5}$ M p-mercuro benzoic acid inhibits the activity of the branching enzyme, which acts specifically on cysteine residue of enzyme protein. No effective activators have been found; the presence of citric acid or glucose-1-phosphoric acid, as described in many reports, is ineffective. All SH-compounds are effective in stabilization of the branching enzyme; the stabilizing effects are in the decreasing order of dithiotreitol, 2-mercaptoethanol, glutathione of reduced-form, cysteine. The presence of 20% glycerol increases the thermal stability of the branching enzyme. Also, the presence of 0.1% calf serum albumin slightly increases the thermal stability, but no stabilizing effect is found with either calcium or magnesium.

(7) Purification:

Purification of the branching enzyme can be carried out similarly as in the case of other enzymes.

(8) Molecular weight:

An ultracentrifugation using sucrose gradient, and gel filtration give a molecular weight of 70,000±20,000.

(9) Crystal structure and elemental analysis: unconfirmed.

(10) Isoelectric point:

Focusing electrophoresis on the branching enzyme gives an isoelectric point of about 4.5.

(11) Disc electrophoresis:

Electrophoresis of the purified branching enzyme, obtained in EXAMPLE A—1 (V), at 4° C. and 2.5 mA per gel for two hours using 7.5% polyacrylamide gel (pH 9.4) gives single enzyme activity peak, wherein the mobility against bromophenol blue is about 0.19.

V. Production of the Bacillus branching enzyme

*Bacillus megaterium* 10-5 strain FERM-P No. 5859 was inoculated in 15 liters of a medium (pH 7.0), consisting of 2.0 w/v % sucrose, 1.0 w/v % polypeptone, 0.5 w/v % meat extract, 0.1 w/v % dipotassium phosphate, 0.1 w/v % sodium chloride, 0.03 w/v % magnesium sulfate, 0.5 w/v % calcium carbonate (sterilized separately) and water, and cultivated at 28° C. for 45 hours under aerobic and stirring conditions. The culture broth was centrifuged at 3,000×g, and the recovered cells were destructed with an ultra-sonicator, followed by centrifugation of the resultant, 10,000×g, obtaining about 1.7 liters of a supernatant containing the branching enzyme (crude enzyme solution). The supernatant contained c.a. 9.6 units of the branching enzyme per ml.

Purification of the branching enzyme thus obtained was carried out as follows. To the supernatant was added ammonium sulfate, and the fraction, obtained in a saturation degree of 0.3–0.65, was collected. The fraction was then dissolved n 10 mM Tris-HCl buffer (pH 7.5), containing 5 mM 2-mercaptoethanol, and the solution was dialyzed against a fresh preparation of the same buffer. The dialyzed enzyme was then applied on DEAE-Sephadex A-50 column (Pharmacia Fine Chemicals AB, Uppsara, Sweden), to absorb the enzyme thereon, and then eluted therefrom with a fresh preparation of the same buffer except that the preparation contained sodium chloride additionally. The enzymatically-active fraction was collected, and dialyzed against a fresh preparation of the same buffer without sodium chloride. The dialyzed enzyme was fractionated with a chromatographic procedure using 4-Aminobutyl Sepharose 4B (Pharmacia Fine Chemicals AB, Uppsara, Sweden), obtaining a purified branching enzyme with a specific activity of about 2,000-fold higher than that before the purification in the yield of about 30% against the starting crude enzyme.

The decrease in iodine-colorization of an amylose with a polymerization degree of 500 on subjecting it to the action of the purified branching enzyme is given in FIG. 4. Also, the increase in iodine-colorization of the resultant product on subjecting it to the action of isoamylase is given in the same Figure.

As obvious from FIG. 4, absorbance at 660 nm declines to about 10% or lower than that without the branching enzyme. Action of isoamylase on the product leads to an about 1.1–10-fold increase in absorbance at 660 nm in comparison with that without isoamylase.

EXAMPLE A-2

*Escherichia coli* branching enzyme

*Escherichia coli* IFO 3366 was inoculated in 1 m³ medium (pH 7.0), consisting of 0.85 w/v % KH₂PO₄, 1.1 w/v % K₂HPO₄, 0.6 w/v % yeast extract, 0.4 w/v % sodium acetate, 0.1 w/v % glucose and water, and cultivated at 37° C. for 16 hours. After completion of the cultivation, the culture broth was centrifuged to collect cells which were then destructed in the presence of glycylglycine buffer (pH 7.5) containing 5 mM dithiotreitol with a homogenizer. After the centrifugation, the supernatant was fractionated with ammonium sulfate, and the fraction, obtained in a saturation range of 30–60%, was collected. The fraction was then dialyzed against 50 mM Tris-HCl buffer (pH 7.5) containing 5 mM dithiotreitol.

Thereafter, the dialyzed enzyme was applied on DEAE-cellulose column to absorb thereon the enzyme which was then eluted therefrom with NaCl gradient (0–0.6 N). The enzymatically-active fraction was collected, and subjected to a membrane filtration, obtaining a concentrated branching enzyme solution in the yield of about 11,000 units.

EXAMPLE A-3

Potato branching enzyme

Ten kg of potato was sliced, and immersed in an aqueous solution containing 0.5 w/v % sodium dithionite and 0.5 w/v % sodium citrate for 30 minutes. Thereafter, the potato slices were crushed with a homogenizer, and the resultant was centrifuged. To the supernatant was added a small amount of an aqueous lead acetate solution to form a precipitate which was then removed by centrifugation. The supernatant was then subjected similarly as in EXAMPLE A-2 to salting-out, dialysis, chromatographic fractionation using DEAE-cellulose and concentration using a membrane filter in the given order, obtaining a branching enzyme solution in the yield of about 900 units.

B. Production of food products

EXAMPLE B-1

"UIRO"

To 460 g "SHIRATAMAKO"—a rice flour, was added 5,000 units of a purified branching enzyme, obtained similarly as in EXAMPLE A-1 (V), in 220 ml water, and the mixture was kneaded sufficiently. Thereafter, the mixture was admixed with 930 g sucrose and 280 g "JOSHINKO"—a rice flour, and kneaded sufficiently.

Then, the resultant was covered in a wet cotton cloth, and steamed for 30 minutes according to conventional methods. The resultant was cooled, cut, and shaped to obtain the titled product, "UIRO"—a type of Japanese-style rice paste confectioneries.

The product is a semi-transparent "UIRO" with an excellent biting property and flavor, and retains its quality over the long period of time because of its low-susceptibility to retrogradation.

EXAMPLE B-2

Bread

To 680 g wheat flour was admixed 4,000 units of a branching enzyme, obtained similarly as in EXAMPLE A-1 (V), and the mixture was added with 20 g sucrose and 11 g NaCl in a small amount of water. After sufficiently kneading the admixture, to the admixture was further added 13 g compressed yeast, 13 g shortening oil, 2 g yeast food and minimum amount of water, and kneaded sufficiently to obtain the dough for the titled product.

Following the conventional method, the dough was fermented at 26° C. for two hours, aged for 15 minutes, and after 15-minute bench-time baked in an oven at about 200° C. for about 40 minutes, obtaining the titled product.

The product is a bread with an excellent flavor and appropriate texture, and retains its quality over a long period.

EXAMPLE B-3

"KAMABOKO"

To 4 kg thawed, minced Alaska pollack meat was admixed 2,000 units of a branching enzyme, obtained similarly as in EXAMPLE A-1 (V), 20 g pullulan in 400 ml ice water, 200 g potato starch, 80 g sucrose, 80 g sodium glutamate, 12 g sodium tripolyphosphate and 120 g NaCl, and the admixture was kneaded sufficiently. The resultant was shaped by the conventional method, and steamed for about 30 minutes at a product temperature of about 80° C.

After cooling at ambient temperature, the resultant was allowed to stand at 4° C. for 24 hours, obtaining the titled product, "KAMABOKO"—a type of Japanese-style fish meat product.

The product is a "KAMABOKO" with a fine texture and excellent gloss and biting properties.

EXAMPLE B-4

Convenient potage soup

One kg of wheat flour was kneaded sufficiently in 360 ml aqueous solution, containing 30 g NaCl and 8,000 units of a branching enzyme, obtained similarly as in EXAMPLE A-1 (V), and the mixture was shaped into strings. The strings were steamed for about two minutes, and heated in a 140°–145° C. oil to effect dehydration, followed by pulverization. The resultant powder was admixed homogenously with 100 g NaCl, 350 g sodium glutamate, 5 g sodium inosinate, 200 g powder milk and 10 g spice, obtaining the titled product.

An addition of 130 ml hot water to 20 g of the product in vessel dissolves readily the product to provide instantly a very delicious potage soup with an appropriate thickness.

EXAMPLE B-5

"MUSHIYOKAN"

To 600 g flour was admixed 250 g "KATAKURI-KO"—a root starch flour from *Erythronium Japonicum*, 20 g NaCl, 400 g "SARASHIAN"—a paste obtained from beans, 1 kg sucrose, 1.4 kg maltose and 2.4 liters of an aqueous solution containing 6,000 units of a branching enzyme, obtained similarly as in EXAMPLE A-2, and the mixture was kneaded sufficiently. The resultant was shaped, and steamed for about forty minutes according to the conventional method, obtaining the titled product, "MUSHIYOKAN"—a type of Japanese-style confectioneries.

The product is excellent in biting properties and flavor, and retains its superior quality over a long period of time because of its low-susceptibility to retrogradation.

EXAMPLE B-6

Custard cream

To 400 g corn starch was admixed 800 units of a branching enzyme in 20 ml aqueous solution, obtained similarly as in EXAMPLE A-3, 1.5 kg of maltose, 1.5 kg of sucrose and 10 g NaCl, and the mixture was further added gradually with 7 kg boiling milk while stirring and heating on a slow fire. The heating was continued until the corn starch gelatinized and the content became semi-transparent. Thereafter, the cooled content was admixed with a small amount of vanilla flavor to obtain the titled product.

The product is a custard cream with an appropriate thickness, and excellent gloss and biting properties, and hardly changes its quality over a long period of time.

Figure 1:
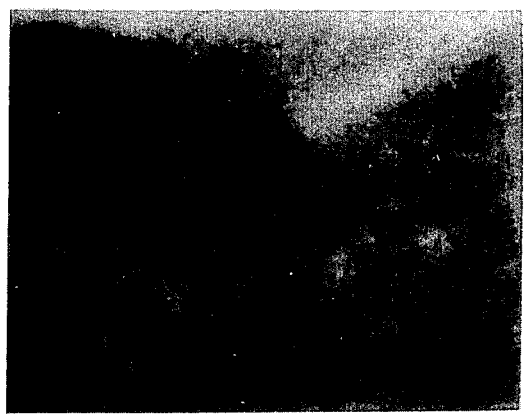
FIG. 1, electro-microphotograph of *Bacillus megaterium* 10–5 strain, ×10,000.
Figure 2:
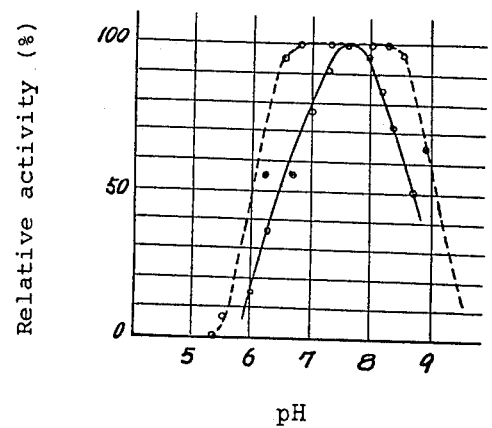
FIG. 2, effect of pH on the enzymatic activity of the branching enzyme, wherein solid line represents the pH optimum, and broken line the pH stability.
Figure 3:
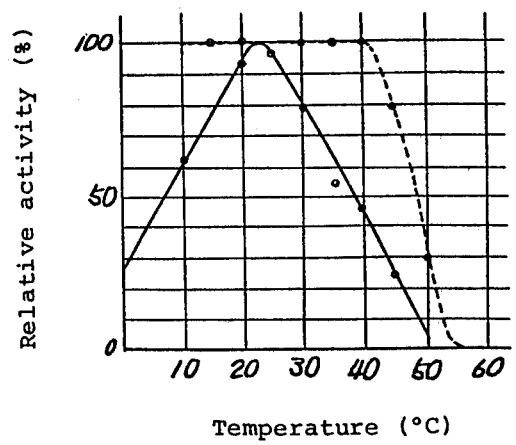
FIG. 3, effect of temperature of the enzymatic activity of the branching enzyme, wherein solid line represents the temperature optimum, and broken line the thermal stability.
Figure 4:
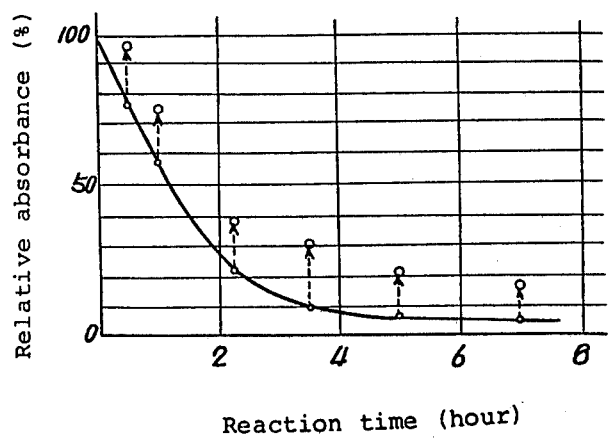
FIG. 4, effect of reaction time on relative absorbance of the reaction mixture, wherein solid line represents the action of the branching enzyme on amylose, and broken line that of isoamylase on the resultant product.

What is claimed is:

1. A process for producing a food product containing an amylaceous substance, comprising:
    preparing an aqueous solution of an amylaceous substance selected from the group consisting of amylose, amylopectin, starch, dextrin and mixtures thereof;
    subjecting the aqueous solution to the action of a branching enzyme (EC 2.4.1.18) for a period sufficient to form substantial branches in the amylaceous substance; and
    preparing a food product containing the resultant branched amylaceous substance.

2. A process in accordance with claim 1, wherein said food product is a confectionary.

3. A process in accordance with claim 1, wherein said food product is a bakery product.

4. A process in accordance with claim 1, wherein said food product is a noddle or pasta.

5. A process in accordance with claim 1, wherein said food product is a fish meat sausage.

6. A process in accordance with claim 1, wherein said food product is a seasoning.

7. A process in accordance with claim 1, wherein said branching enzyme is a member selected from the group consisting of *Bacillus megaterium* branching enzyme, *Escherichia coli* branching enzyme and potato branching enzyme.

8. A process in accordance with claim 1, wherein said branching enzyme is that which is produced by *Bacillus megaterium* 10–5 FERM-P No. 5859 strain.

9. A process for producing a food product containing an amylaceous substance, comprising:
    preparing an aqueous suspension of a branching enzyme (EC 2.4.1.18) and an amylaceous substance selected from the group consisting of amylose, amylopectin, starch, dextrin and mixtures thereof;

heating said aqueous suspensions at a temperature at which said enzyme is substantially stable for a period sufficient to form substantial branches in the amylaceous substance; and preparing a food product containing the resultant branched amylaceous substance.

10. A process in accordance with claim 9, wherein said food product is a confectionary.

11. A process in accordance with claim 9, wherein said food product is a bakery product.

12. A process in accordance with claim 9, wherein said food product is a noodle or pasta.

13. A process in accordance with claim 9, wherein said food product is a fish meat sausage.

14. A process in accordance with claim 9, wherein said food product is a seasoning.

15. A process in accordance with claim 9, wherein said branching enzyme is a member selected from the group consisting of *Bacillus megaterium* branching enzyme, *Escherichia coli* branching enzyme and potato branching enzyme.

16. A process in accordance with claim 9, wherein said branching enzyme is that which is produced by *Bacillus megaterium* 10-5 FERM-P No. 5859 strain.

17. In a process for producing a food product containing an amylaceous substance wherein said food product has added thereto or is prepared with an amylaceous substance selected from the group consisting of amylose, amylopectin, starch, dextrin, and mixtures thereof the improvement comprising subjecting said amylaceous substance to the action of a branching enzyme (EC 2.4.1.18) for a period sufficient to form substantial branches in the amylaceous substance prior to the completion of preparation of the product, whereby the qualities of the food product, including shelf life, are improved.

* * * * *